US007982031B2

(12) United States Patent
Kowalczyk et al.

(10) Patent No.: US 7,982,031 B2
(45) Date of Patent: Jul. 19, 2011

(54) METHOD FOR SELECTIVE CARBOHYDRATE OXIDATION USING SUPPORTED GOLD CATALYSTS

(75) Inventors: Jörg Kowalczyk, Eisenberg/Steinborn (DE); Alireza Haji Begli, Ramsen (DE); Ulf Prüsse, Braunschweig (DE); Heinz Berndt, Berlin (DE); Irene Pitsch, Berlin (DE)

(73) Assignee: Sudzucker Aktiengesellschaft, Mannheim/Ochsenfurt (DE)

( * ) Notice: Subject to any disclaimer, the term of this patent is extended or adjusted under 35 U.S.C. 154(b) by 219 days.

(21) Appl. No.: 10/555,714

(22) PCT Filed: May 4, 2004

(86) PCT No.: PCT/EP2004/004703
§ 371 (c)(1),
(2), (4) Date: Jul. 27, 2006

(87) PCT Pub. No.: WO2004/099114
PCT Pub. Date: Nov. 18, 2004

(65) Prior Publication Data
US 2007/0112186 A1 May 17, 2007

(30) Foreign Application Priority Data

May 5, 2003 (DE) ................................ 103 19 917

(51) Int. Cl.
*C07H 1/00* (2006.01)
*C07H 3/00* (2006.01)
*C08B 37/00* (2006.01)
(52) U.S. Cl. ...................................................... 536/124
(58) Field of Classification Search .................. None
See application file for complete search history.

(56) References Cited

U.S. PATENT DOCUMENTS

| | | | |
|---|---|---|---|
| 3,862,005 A | 1/1975 | Miyake et al. | |
| 4,985,553 A | 1/1991 | Fuertes et al. | 536/124 |
| 5,132,452 A | 7/1992 | Deller et al. | 562/531 |
| 6,548,682 B1 | 4/2003 | Weisbeck et al. | 549/523 |

FOREIGN PATENT DOCUMENTS

| | | |
|---|---|---|
| DE | 43 07 388 A1 | 9/1994 |
| DE | 198 04 709 A1 | 8/1999 |
| GB | 1 325 727 | 8/1973 |
| JP | 55-20679 | 6/1980 |
| JP | 06-007184 | 1/1994 |
| JP | 8-509701 | 10/1996 |
| WO | WO 00/59633 | 10/2000 |

OTHER PUBLICATIONS

IT 1313696 B1, Chem. Abstr. (Online). In:STN. Accession No. 2002:872740.
S. Biella et al. "Application of gold catalysts to selective liquid phase oxidation". In:Catalysis Today, ISSN 0920-5861, 2002 vol. 72 S. 43-49.
S.Biella et al. "Selective Oxidation of D-Glucose on Gold Catalyst", In: Journal of Catalysis, ISSN 0021-9517, 2002, vol. 206, S.242-247.
J.Falbe et al. "Rompp Chemie Lexikon-Band 3: H-L", 10. Auflage, Georg Thieme Verlag Stuttgart, New York, ISBN 3-13-734810-2, 1997, Seite 2329f. Begrif Lactobionsäure.
Chemical Abstracts: registry-Datenbank (online). In: STN. Registry Nos. 43043-56-7 und 534-42-9.
International Search Report PCT/EP2004/004703 dated Aug. 24, 2004.
English translation of Russian Official Action dated Oct. 16, 2007 relating to Russian Application No. 2005137687/43(042094).
English translation of Russian Official Action dated Mar. 7, 2008 relating to Russian Application No. 2005137687/43(042094).
H. Berndt et al. "Oxygen adsorption on $Au/Al_2O_3$ Catalysts and relation to the catalytic oxidation of ehtylene glycol to glycolic acid", Applied Catalysis A: General 6442 (2003) 1-11.
Laura Prati et al. "Gold on carbon as a new catalyst for selective liquid phase oxidation of diols", Journal of Catalysis 176, 552-560 (1998) Article No. CA982078.
G. Martra et al. "Highly dispersed $Au/SiO_2$ catalyst obtained by deposition of gold Sols derived from $Au(PPh_3)C1$", Symposium 19 Catalysis by Silver and Gold, 19-P-03, EuropaLat V, Sep. 2001, Limerick, Ireland.
G.J. Feldmeyer et al. "Metal loaded diblockcopolymer micelled for preparing $Au/TiO_2$ catalysts for the selective CO oxidation in $H_2$-rich gas", $4^{th}$ World Congress on Oxidation Catalysis, Sep. 16-21, 2001 pp. 47-48, Berlin/Postdam—Germany, Book of Extended Abstracts vol. 1, Dechema e.V. Subject Division Catalysis.
Laura Prati et al: "Selective liquid phase oxidation using gold catalysts", Heterogeneous Catalysis and Fine Chemicals V, Aug.-Sep. 1999, Lyon.
Laura Prati et al: "Chemoselective catalytic oxidation of polyols with dioxygen on gold supported catalysts", $3^{rd}$ World Congress on Oxidation Catalysis, 1997, pp. 509-516, R.K. Grasseli, et al. and J.E. Lyons (Editors)—Elsevier Science B.V.
Laura Prati et al: "New gold catalysts for liquid phase oxidation", Gold Bulletin 1999, 32(3), pp. 96-101. Silvio Carrettin et al: "Selective oxidation of glycerol to glyceric acid using a gold catalyst in aqueous sodium hydroxide", Chem Commun (The Royal Society of Chemistry) 2002, 696-697.
Jan Dierk Grunwaldt et al: "Preparation of supported gold catalysts for low-temperature CO oxidation via "size-controlled" gold colloids", Journal of Catalysis 181, 223-232 (1999).
Yannick Guari et al: "In situ formation of gold nanoparticles within functionalised ordered mesoporous silica via an organometallic 'chimie douce' approach", Chem. Commun., 2001, 1374-1375 (The Royal Society of Chemistry).
Masatake Haruta: "Size-and support-dependency in the catalysis of gold", Catalysis Today 36 (1997) 153-166.
Masatake Haruta: "Catalysis of gold nanoparticles deposited on metal oxides", Feature, Cat. Tech., vol. 6, No. 3, 2002 pp. 102-115.

(Continued)

*Primary Examiner* — Layla Bland
(74) *Attorney, Agent, or Firm* — Ostrolenk Faber LLP

(57) ABSTRACT

The present invention relates to a method for the selective oxidation of a carbohydrate in the presence of a gold catalyst which includes nanodispersed gold particles on a metal oxide support, to a method for the selective oxidation of an oligosaccharide in the presence of a gold catalyst which comprises nanodispersed gold particles on a carbon or metal oxide support, and to the aldonic acid oxidation products prepared by use of these methods.

48 Claims, 5 Drawing Sheets

OTHER PUBLICATIONS

S. Tsubota et al: "Preparation of nanometer gold strongly interacted with $TiO_2$ and the structure sensitivity in low-temperature oxidation of $CO^{2}$", Preparation of Catalysts VI, 1995, pp. 227-232, Scientific Basis for the Preparation of Heterogeneous Catalysts, G. Poncelet et al. (Editors), Elsevier Science B.V.

Susumu Tsubota et al: "Preparation of highly dispersed gold on titanium and magnesium oxide", Preparation of Catalysts V, 1991, pp. 695-696, G. Poncelet et al. (Editors) Elsevier Science Publishers B.V., Amsterdam-Printed in the Netherlands.

Caixia Qi et al: "Epoxidation of propylene over gold catalysts supported on non-porous silica", Applied Catalysis A: general 218 (2001) 81-89.

Y. Önal et al: "Oxidation von glukose an gold/trager-katalysatoren" XXXV. Jahrestreffen Deutscher Katalytiker, Mar. 20-22, 2002, Weimar, Tagungsband, pp. 284-286.

F. Porta et al: "Metal sols as a useful tool for heterogenous gold catalyst preparation: reinvestigation of a liquid phase oxidation", Catalysis Today 61 (2000) 165-172.

Anke Wolf et al: "A systematic study of the synthesis conditions for the preparation of highly active gold catalysts", Applied Catalysis A: General 226 (2002) 1-13.

Nikhil R. Jana et al: "Seeding growth for size control of 5-40 nm diameter gold nanoparticles", Langmuir 2001, 17, 6782-6786.

Peter Claus et al: "Supported gold nanoparticles from quantum dot mesoscopic size scale: Effect of electronic and structural properties on catalytic hydrogenation of conjugated functional groups", J. Am. Chem. Soc. 2000, 122, 11430-11439.

Yoshio Kobayashi et al: "Sol-gel processing of silica-coated gold nanoparticles", Langmuir 2001, 17, 6375-6379.

English translation of XXXVth Annual Meeting of German Catalysis Scientists, Mar. 20-22, 2002, Weimar Conference Proceedings.

Fokko R. Venema, et al., "Platinum-catlyzed Oxidation of Aldopentoses to Aldaric Acids", Journal of Molecular Catalysis, 77 (1992) 75-85.

§9.2 , "Oxidation of Alcohols and Aldehydes on Metal Catalysts ", Fine Chemicals Through Heterogeneous Catalysis, eds. R.A. Sheldon and H.v. Bekkum, Wiley-VCH (2001).

§9.3, "Oxidation of Carbohydrates on Metal Catalysts", Fine Chemicals Through Heterogeneous Catalysis, eds. R.A. Sheldon and H.v. Bekkum, Wiley-VCH (2001).

Japanese Office Action mailed Dec. 15, 2009 in corresponding Japanese Patent Application No. 2006-505363 (in English language).

S. Biella, et al. "Application of Gold Catalysts to Selective Liquid Phase Oxidation," Catalysis Today, vol. 72, 2002, pp. 43-49.

Prati et al. "Chemoselective Catalytic Oxidation of Polyols With Dioxygen On Gold Supported Catalysts," Studies in Surface Science and Catalysis, vol. 110 and 509-516 (1997).

METHOD FOR SELECTIVE CARBOHYDRATE OXIDATION USING SUPPORTED GOLD CATALYSTS

CROSS REFERENCE TO RELATED APPLICATIONS

The present application is a 35 U.S.C. §371 National Phase conversion of PCT/EP2004/004703 filed May 4, 2004, which claims priority of German Application No. 103 19 917.9 filed May 5, 2003. The PCT International Application was published in the German language.

FIELD OF THE INVENTION

The present invention relates to a method for selective oxidation of a carbohydrate in the presence of a gold catalyst which comprises nanodispersed gold particles on a metal oxide support, to a method for the selective oxidation of an oligosaccharide in the presence of a gold catalyst which comprises nanodispersed gold particles on a carbon or metal oxide support, and to the aldonic acid oxidation products prepared using these methods.

BACKGROUND OF THE INVENTION

About 1.2 million metric tons of lactose each year result as waste product from the manufacture of cheese and in the whey-processing industry around the world. However, lactose as the principal carbohydrate constituent of milk has scarcely any economic importance as yet. One of the reasons for this is to be found in the lactose intolerance of some of the population. People with lactose intolerance are unable to utilize lactose and respond to consumption of lactose with symptoms of intolerance such as diarrhea. Only a relatively small part of the resulting lactose is utilized commercially, with lactose being employed for example as fermentation substrate, as filler or for the manufacture of dietary food products. Most of the resulting amounts of lactose are, however, disposed of through the manufacturers' waste-water treatment plants, possibly leading to disturbances of the ecological balance in water courses. However, since lactose is a raw material which is available in large quantities and at extremely reasonable cost, there is great interest in adding economic value to this carbohydrate. For this reason, various enzymatic cleavage and transformation reactions in which lactose is employed as starting material for manufacturing higher-value products in particular have recently been developed.

It is thus possible by oxidizing lactose to obtain lactobionic acid which is of great interest for a number of applications. The method employed to date for preparing lactobionic acid from lactose is an enzymatic one using the enzymes cellobiose dehydrogenase and hexose oxidase. The unsatisfactory conversion for example in the reaction catalyzed by cellobiose dehydrogenase can be increased by using the enzyme laccase which reoxidizes the redox mediators which are reduced in the reaction. Because of its excellent ability to form metal chelates, lactobionic acid is employed inter alia in the so-called Wisconsin transplantation solution, because lactobionic acid is able to reduce the oxidative damage, caused by metal ions, during storage of organs for transplantation. Lactobionic acid can likewise be employed as biodegradable cobuilder in washing powder, which may comprise up to 40% lactobionic acid. Because of the mild sweet-sour taste of lactobionic acid there are further possible applications in food technology.

There is also great potential for use of other aldonic acids or oligosaccharide aldonic acids in the pharmaceutical industry, the manufacture of cosmetics and in food technology. Aldonic acids are currently prepared mainly by microbial or enzymatic conversion from the corresponding mono- or oligosaccharides. Thus, for example, glucose can be converted into gluconic acid by using *Acetobacter methanolicus*. The enzymatic preparation of aldonic acids is, however, generally characterized by a relatively low productivity and is also not without problems for environmental protection reasons. There is thus a great interest in alternative oxidation methods leading to distinctly less environmental pollution, where the carbohydrate to be oxidized, for example a monosaccharide, is oxidized to the corresponding aldonic acid using a heterogeneous catalyst.

Heterogeneous catalysis of an oxidation reaction normally takes place in a three-phase reactor, with the solid catalyst, usually in powder form, being suspended in a liquid phase comprising the compound to be oxidized, and oxygen being bubbled through the liquid phase during the reaction. Although catalytic oxidation has some considerable advantages by comparison with the enzymatic reaction, especially in relation to considerably less environmental pollution, it does have a decisive disadvantage. When metals are used, activation of dioxygen may lead to free-radical reactions which may, especially in the case of polyfunctional molecules, distinctly reduce the selectivity of the conversion (Sheldon and Kochi, "Metal Catalyzed Oxidations of Organic Compounds", 1981, Academic Press, New York).

The use of supported palladium and platinum catalysts for oxidizing glucose has been investigated most thoroughly to date. It has emerged from this that on use of these catalysts there are considerable limitations on the catalytic conversion of glucose into gluconic acid because of the low selectivity and reaction rate. Moreover, deactivation of both types of catalyst is relatively rapid. This deactivation is evidently derived either from blocking of the catalyst surface owing to adsorption of molecules or from poisoning effects caused by dioxygen (Van Dam, Kieboom and Van Bekkum, Appl. Catal., 33 (1990), 187). Some of the factors which limit the catalytic conversion of glucose to gluconic acid can be distinctly improved by introducing promoters such as bismuth or lead. Besides an improvement in the catalyst life, in particular the reaction selectivity and the reaction rate are increased thereby (Fiege and Wedemeyer, Angew. Chem., 93 (1981), 812; Wenkin et al., Appl. Catal. A: General, 148 (1996), 181).

However, there is controversy about Pd and Bi because of possible leaching of these toxicologically objectionable substances. Slightly alkaline conditions are necessary to increase the reaction rate and to prevent catalyst deactivation. However, side reactions which reduce gluconate production occur under such conditions. It is likewise disadvantageous that gluconate is produced instead of free gluconic acid on use of bases (Biella, Prati and Rossi, Journal of Catalysis, 206 (2002), 242-247).

For these reasons, the fermentation process is still preferred for industrial production of gluconic acid, despite the problems arising with this method, for example the heavy contamination of waste water and the not inconsiderable formation of by-products. This is why there is a need to develop novel types of catalysts which make catalytic oxidation of carbohydrates possible for preparing aldonic acids using dioxygen as oxidizing agent, and having a long useful life besides high activity and selectivity.

Supported gold catalysts have been employed to date in particular for oxidizing CO or propene in the gas phase and for selective hydrogenations. Biella et al., Journal of Catalysis, 206 (2002) 242-247, describe the use of a carbon-supported gold catalyst for selective oxidation of D-glucose to D-gluconic acid in the liquid phase. Comparison between the carbon-supported gold catalyst and conventional palladium and platinum catalysts shows that the gold catalyst is superior in several respects to both palladium and platinum catalysts. In particular, compared with palladium and platinum catalysts, the gold catalyst used is substantially more stable to deactivation. A further advantage of the gold catalyst used is that no external pH monitoring thereof is necessary in the glucose conversion. The carbon-supported gold catalysts used do, however, have a considerable disadvantage. On the one hand, the leaching of gold out of the catalyst increases as the pH falls. On the other hand, growth of the gold particles is promoted as the pH rises. Both lead to a decrease in the catalyst activity. The increasing dissolution of gold particles as the pH rises is associated with an enlargement of the gold particles. This is probably attributable to the fact that small gold particles dissolve and then the gold is deposited on larger gold particles, resulting in a reduction of Au(I,III) particles.

SUMMARY OF THE INVENTION

The technical problem on which the present invention is based is to provide gold catalysts which are improved by comparison with the catalysts known in the art and which have a high selectivity and activity in relation to the oxidation of carbohydrates to the corresponding aldonic acids, and with which the problems of gold catalysts which are known in the art, especially the decline in activity which is caused by multiple use and whose extent depends on the pH, do not occur, so that the gold catalysts can be employed for the industrial preparation of aldonic acids from suitable carbohydrate starting materials. It is additionally intended that it be possible to employ the improved gold catalysts for oxidizing a large number of different carbohydrates to the corresponding aldonic acids.

The present invention solves the technical problem on which it is based by providing a method for the selective oxidation of at least one carbohydrate, a carbohydrate mixture or a composition having a content thereof, where an aqueous solution of the carbohydrate, of the mixture or of the composition is reacted in the presence of a gold catalyst comprising nanodispersed gold particles on a metal oxide support, and of oxygen, especially dioxygen.

The metal oxide-supported gold catalysts employed according to the invention for carbohydrate oxidation are notable for making the selective oxidation of a large number of carbohydrates possible, especially carbohydrates whose C1 carbon atom has an oxidizable aldehyde group, or can be provided with an oxidizable aldehyde group, to the corresponding aldonic acids. Compared with conventional platinum and palladium catalysts, the gold catalysts used according to the invention show an activity for selective carbohydrate oxidation which is up to an order of magnitude higher. This high activity is all the more remarkable since the metal loading of the gold catalysts is considerably less than for platinum or palladium catalysts. In addition, the metal oxide-supported gold catalysts used according to the invention show a considerably increased selectivity for aldonic acid production compared with platinum and palladium catalysts, meaning that the selectivity for other oxidation products is distinctly reduced. Whereas the use of platinum and palladium catalysts always results in a product mixture that, besides the desired aldonic acid, comprises a large number of other oxidation products derived from the oxidation of, for example, alcohol groups, the use of the metal oxide-supported gold catalysts employed according to the invention results in a virtually pure aldonic acid which comprises no other detectable oxidation products or even extremely small amounts thereof. The exceptionally high selectivity of the metal oxide-supported gold catalysts employed according to the invention is attributable in particular to the fact that only the aldehyde group of the C1 carbon atom is oxidized, but not alcohol groups.

The metal oxide-supported gold catalysts employed according to the invention are distinguished from carbon-supported gold catalysts by having a considerably longer useful life. Whereas a relatively marked decline in activity has been observed after use of carbon-supported gold catalysts only once or twice (Biella et al., J. Catalysis, 206 (2002), 242-247), the metal oxide-supported gold catalysts can be used at least 20 times with a negligible decline in the catalyst activity and selectivity of the oxidation. The metal oxide-supported catalysts employed according to the invention can therefore advantageously be employed for the industrial preparation of aldonic acids. A further advantage of the metal oxide-supported gold catalysts employed according to the invention is that they can be employed for the oxidation of a large number of different initial carbohydrate substrates, for example monosaccharides, oligosaccharides or mixtures thereof. It is advantageously possible to oxidize both aldoses and ketoses.

DETAILED DESCRIPTION OF PREFERRED EMBODIMENTS OF THE INVENTION

In connection with the present invention, a "catalyst" means a substance which can reduce the activation energy required for a particular reaction to proceed, and thus increase the reaction rate, without appearing in the final product of the reaction. A "gold catalyst" means a catalyst which comprises gold on a support material or which consists of gold on a support material, where the gold is present in the form of dispersed nanoparticles on the support. The gold nanoparticles have a diameter of less than 20 nm, preferably of <10 nm and particularly preferably of <5 nm.

A "metal oxide support" means in connection with the present invention a catalyst support which consists of at least one oxide of a main group or transition metal or metalloid, including compounds which comprise more than one metal and/or metalloid. Preference is given in this connection to oxides of metals or metalloids of main group 2 of the PTE such as MgO, CaO or BaO, oxides of metals or metalloids of main group 3 of the PTE such as $Al_2O_3$ or lanthanoid oxides or oxides of metals or metalloids of main group 4 of the PTE such as $SiO_2$, $TiO_2$, $SnO_2$ or $ZrO_2$. The compounds having more than one metal and/or metalloid are preferably silicates, especially aluminosilicates.

A preferred embodiment of the invention relates to the use of a gold catalyst for oxidizing carbohydrates, where the catalyst comprises nanodispersed gold particles on an $Al_2O_3$ support. The $Al_2O_3$-supported gold catalyst comprises according to the invention about 0.1% to 5% gold, preferably about 0.5% to 1% gold. The $Al_2O_3$-supported gold catalyst employed according to the invention for the selective oxidation of carbohydrates preferably comprises gold nanoparticles having a diameter of <10 nm, particularly preferably of <6 nm and most preferably of from 1 to 2 nm.

A preferred embodiment of the invention relates to the use of a gold catalyst for oxidizing carbohydrates, where the catalyst comprises nanodispersed gold particles on a $TiO_2$ support. The $TiO_2$-supported gold catalyst comprises according to the invention about 0.1% to 5% gold, preferably about 0.5% to 1% gold, particularly preferably about 0.5% gold.

The TiO$_2$-supported gold catalyst employed according to the invention for the selective oxidation of carbohydrates preferably comprises gold nanoparticles having a diameter of <20 nm, particularly preferably of <6 nm and most preferably of from 1-4 nm.

The metal oxide-supported gold catalysts used according to the invention can be prepared, i.e. gold can be deposited in the form of nanoparticles on the metal oxide support materials, for example by employing precipitation methods where the gold is deposited in the form of oxidic/hydroxic gold precursors by precipitation on the metal oxide support, or is precipitated together with a precursor of the metal oxide support. Au can also be introduced in the sol-gel synthesis of the support, for example of an earth metal oxide or a transition metal oxide. Also known are impregnation with gold solutions and the application of Au colloids to supports using various polymers as colloid stabilizers. Suitable methods for preparing metal oxide-supported gold catalysts include for example precipitation methods, deposition-precipitation methods and methods for chemical deposition from the gas phase (CVD methods) and are described inter alia in Prati and Martra, Gold Bulletin, 32(3) (1999), 96-101; Wolf and Schüth, Applied Catalysis A: General., 226 (2202), 1-13, and Berndt et al., Applied Catalysis A: General, 6442 (2003), 1-11, the disclosure of these publications being included by reference completely in the disclosure of the present invention.

The metal oxide-supported catalyst used according to the invention for carbohydrate oxidation is employed in a heterogeneous catalysis. This means that the catalyst is in the form of a solid, whereas the carbohydrates to be oxidized are present in liquid phase, for example as aqueous solution. The dioxygen employed for carbohydrate oxidation is then bubbled as gas through the liquid phase and is distributed and dissolved in the liquid phase by vigorous agitation.

For the inventive selective oxidation of carbohydrates, carbohydrate mixtures or compositions with a content thereof, the metal oxide-supported gold catalyst is preferably employed in the form of a powder or granules.

The "selective oxidation of carbohydrates" means in particular the oxidation of an oxidizable aldehyde group on the C1 carbon of a carbohydrate to a carboxyl group, whereas alcohol groups on other carbon atoms of the carbohydrate are not oxidized. The result of the inventive selective oxidation of the carbohydrate is therefore preferably an aldonic acid. In connection with the present invention, an "aldonic acid" means a saccharic acid obtained by oxidizing an aldehyde group of a carbohydrate. Aldonic acids are able to form γ- or δ-lactones through elimination of water. Free aldonic acids are present in equilibrium with lactones.

In connection with the present invention, "carbohydrates" mean polyhydroxy aldehydes and polyhydroxy ketones, and high molecular weight compounds which can be converted by hydrolysis into such compounds. The term "carbohydrate" also includes derivatives of a carbohydrate which are formed from the carbohydrate in one or more reaction steps. The carbohydrates employed according to the invention are preferably aldoses having an oxidizable aldehyde group at the C1 carbon, or 2-ketoses where an oxidizable aldehyde group can be introduced at the C1 carbon atom.

In connection with the present invention, an "aldose" means a carbohydrate which has an aldehyde group (—CHO) and at least one center of asymmetry, the numbering of the aldose chain starting at the carbon atom that comprises the aldehyde group. Selective oxidation of the aldehyde group of an aldose results in an aldonic acid. Selective oxidation of a mixture of aldoses therefore results in a mixture of different aldonic acids.

The present invention therefore relates to a method for preparing an aldonic acid or a mixture of various aldonic acids by selective oxidation of one or more aldoses having an oxidizable aldehyde group by using a metal oxide-supported gold catalyst.

In connection with the present invention, a "ketose" means a carbohydrate that comprises a keto group. If the keto group is in position 2, the compound is a 2-ketose. Ketoses show mutarotation as a result of the formation of anomers. Although ketoses cannot in general be oxidized, it is possible to convert 2-ketoses into aldoses, in which case the 2-ketose is initially converted into the corresponding enol form which is then isomerized to an oxidizable aldose, in which case the —OH group on the C1 carbon atom becomes the carbonyl group, and the C=O group originally present on the C2 carbon atom becomes an HC—OH group. This entails from a purely formal viewpoint a shift of the carbonyl group from the $C_2$ to the $C_1$ position.

The present invention therefore also relates to a method for preparing an aldonic acid or a mixture of various aldonic acids by use of one or more 2-ketoses, where the 2-ketose(s) is/are initially converted into the tautomeric aldose form(s) having an oxidizable aldehyde group, and then selectively oxidized by use of a metal oxide-supported gold catalyst.

The carbohydrates to be oxidized include according to the invention both monomeric polyhydroxy aldehydes or polyhydroxy ketones, i.e. monosaccharides, their dimers to decamers, meaning oligosaccharides such as disaccharides, trisaccharides etc., and the macromolecular polysaccharides. "Monosaccharides" mean in connection with the present invention compounds of the general chemical formula $C_nH_{2n}O_n$ having 2 to 6 oxygen functions, with natural monosaccharides being essentially hexoses and pentoses. The carbon chain of a monosaccharide may be unbranched or branched. "Oligosaccharides" mean compounds which are obtained by combining 2 to 10 monosaccharide molecules with elimination of water and which are glycosides or ethers. In connection with the present invention, "polysaccharides" mean essentially two groups of substances, namely on the one hand compounds which serve as structural materials for plants and some animals, and on the other hand compounds which serve as reserve materials for simple carbohydrates and are released by particular enzymes when required in the body. Polysaccharides include both homoglycans and heteroglycans.

In connection with the present invention, a "carbohydrate mixture" means a mixture of two or more chemically different carbohydrates which preferably comprises no constituents other than carbohydrates and which is formed without previous chemical reaction. The carbohydrate mixture to be oxidized may be either a homogeneous mixture or a heterogeneous mixture. A heterogeneous mixture consists of at least two phases which comprise the individual carbohydrate components or which consist of the individual carbohydrate components. A homogeneous mixture comprises a molecular dispersion of the individual carbohydrate components with one another, without an interfaces being present between the individual components, it being possible for the individual carbohydrate components to be present in any quantitative ratios. If the mixture to be oxidized is not in liquid form, or if the mixture to be oxidized comprises a solid phase, the mixture is converted according to the invention into the liquid phase, for example by preparing an aqueous solution, before the selective oxidation.

One embodiment of the invention relates to the use of a carbohydrate mixture to be oxidized as initial substrate, in which at least one carbohydrate constituent comprises a C1 carbon atom having an oxidizable aldehyde group, or in which the C1 carbon atom of at least one carbohydrate constituent can be provided with an oxidizable aldehyde function before the selective oxidation.

A preferred embodiment of the invention relates to the use of a carbohydrate mixture to be oxidized as initial substrate, in which either a plurality, particularly preferably all of the carbohydrate constituents comprise a C1 carbon atom having an oxidizable aldehyde group, or in which the C1 carbon atom of a plurality, particularly preferably of all of the carbohydrate constituents can be provided with an oxidizable aldehyde function before the oxidation. The carbohydrate mixture to be oxidized thus preferably comprises a plurality of carbohydrates which either already have an oxidizable aldehyde group at their C1 carbon or an oxidizable aldehyde group can be introduced at their C1 carbon atom before the selective oxidation. In this embodiment, the carbohydrate mixture to be oxidized may thus include a plurality of different aldoses and/or 2-ketoses. The carbohydrate mixture to be oxidized particularly preferably consists exclusively of individual carbohydrate components which either already have an oxidizable aldehyde group at their C1 carbon or an oxidizable aldehyde group can be introduced at their C1 carbon atom before the oxidation. In this embodiment, the carbohydrate mixture to be oxidized therefore consists exclusively of different aldoses and/or 2-ketoses.

In connection with the present invention, a "composition comprising at least one carbohydrate or a carbohydrate mixture" means a mixture of different chemical compounds, where at least one constituent of the composition is a carbohydrate whose C1 carbon atom has a free aldehyde group, or can be provided with an oxidizable aldehyde group before the oxidation. The other constituents of the composition to be oxidized may be for example other, non-oxidizable carbohydrates, proteins, pectins, acids, fats, salts, flavorings such as vanillin or furfurals, etc. or mixtures thereof. The composition to be oxidized may of course include a plurality of different aldoses and/or 2-ketoses.

The present invention therefore relates to the selective oxidation of a carbohydrate, of a mixture of different carbohydrates or of a composition with a content thereof by using a metal oxide-supported gold catalyst, where the carbohydrates are preferably monosaccharides or oligosaccharides.

In a preferred embodiment of the invention, the monosaccharide to be oxidized is an aldose such as glucose, galactose, mannose, xylose or ribose. The oxidation of glucose by using the method of the invention results in gluconic acid as oxidation product. Oxidation of galactose by using the method of the invention results in galactonic acid as oxidation product.

In a further particularly preferred embodiment, the carbohydrate to be oxidized is an oligosaccharide, in particular a disaccharide. The disaccharide to be oxidized is preferably a disaccharide aldose such as maltose, lactose, cellobiose or isomaltose. The selective oxidation of maltose according to the invention by use of the method of the invention results in maltobionic acid as oxidation product. Lactose oxidation using the method of the invention results in lactobionic acid as oxidation product.

In a further particularly preferred embodiment of the invention, a disaccharide ketose is employed as oligosaccharide to be oxidized. The disaccharide ketose to be oxidized is preferably palatinose (isomaltulose). Before the oxidation, palatinose is converted according to the invention into the tautomeric aldose form, which is then oxidized.

In a further particularly preferred embodiment of the invention, the carbohydrate to be oxidized is a maltodextrin. Maltodextrins are water-soluble carbohydrates obtained by enzymatic degradation of starch, in particular dextrose equivalents having a chain length of from 2 to 30, preferably 5 to 20, anhydroglucose units and a proportion of maltose. Selective oxidation of maltodextrin by use of the method according to the invention results in an oxidation product which has according to the invention, in accordance with the composition, besides the oligosaccharide aldonic acids a proportion of maltobionic acid and gluconic acid.

In a further particularly preferred embodiment, the carbohydrate mixture to be oxidized or the carbohydrate composition to be oxidized is a starch syrup. A starch syrup means glucose syrup which is obtained from starch and is in the form of a purified aqueous solution, where the dry matter amounts to at least 70%.

In a further embodiment, the carbohydrate to be oxidized is a furfural. The furfural to be oxidized is preferably hydroxymethylfurfural (HMF) or glycosyloxymethyl-furfural (GMF).

In a preferred embodiment of the method of the invention for selective carbohydrate oxidation, an aqueous solution of the carbohydrate or carbohydrate mixture to be oxidized or of a composition having a content thereof is prepared and comprises the carbohydrate or the carbohydrate mixture in an amount of at least about 10 mmol/l, preferably at least about 100 mmol/l, 150 mmol/l, 200 mmol/l or 250 mmol/l and most preferably at least about 1000 mmol/l or 1500 mmol/l. Subsequently, the metal oxide-supported gold catalyst, preferably in powder form, is added in an amount of about 100 mg/l to 10 g/l to the aqueous carbohydrate solution, preferably employing about 1 g of catalyst per liter. The ratio between the amount of the carbohydrate(s) to be oxidized or of the carbohydrate mixture and the amount of the gold present on the metal oxide support is according to the invention at least about 300, more preferably more than 350, 500, 1000, 1500, 2000, 2500, 3000, 3500 or 4000 and most preferably more than 9000, 10 000, 15 000, 20 000, 25 000, 30 000, 35 000 or 40 000.

In a preferred embodiment of the method of the invention for selective carbohydrate oxidation, the selective oxidation of the at least one carbohydrate, of the carbohydrate mixture or of the composition having a content thereof is carried out at a pH of from 7 to 11, preferably 8 to 10. The temperature employed for carrying out the carbohydrate oxidation according to the invention is from 20° C. to 140° C., preferably 40° C. to 90° C., particularly preferably 50° C. to 80° C. The pressure according to the invention is about 1 bar to about 25 bar. During the oxidation, according to the invention oxygen and/or air is bubbled through the aqueous solution of the carbohydrate, of the mixture or of the composition at a gas input rate of from 100 ml/(min×$L_{reactor\ volume}$) to 10 000 ml/(min×$L_{reactor\ volume}$), preferably of 500 ml (min× $L_{reactor\ volume}$).

The technical problem on which the present invention is based is also solved by a method for the selective oxidation of at least one oligosaccharide, a mixture thereof or a composition having a content thereof, where an aqueous solution of the oligosaccharide, of the mixture or of the composition is reacted in the presence of a gold catalyst comprising nanodispersed gold particles on a support, and of oxygen.

The invention thus provides for a gold catalyst which includes nanodispersed gold particles on a support, where the support is either a metal oxide support or a carbon support, to be employed for selective oxidation of oligosaccharides.

In a preferred embodiment of the invention, a carbon-supported gold catalyst is employed for selective oxidation of an oligosaccharide, of an oligosaccharide mixture or of a composition having a content thereof.

A "carbon support" means in connection with the present invention in particular an activated carbon support. The carbon-supported gold catalysts employed according to the invention are preferably prepared by using the incipient wetness method or via gold sols. Suitable methods for preparing carbon-supported gold catalysts include in particular suitable impregnation techniques and gold colloid application to a support, for example by use of specific polymers. Suitable methods for preparing carbon-supported gold catalysts are described for example in Prati and Martra, Gold Bulletin, 32(3) (1999), 96-101, the disclosure of this publication being included by reference completely in the disclosure of the present invention. The carbon-supported gold catalysts employed according to the invention have in particular nanoparticles having a diameter of less than 20 nm, preferably of <10 nm, particularly preferably of <6 nm and most preferably of <2 nm. The carbon-supported gold catalysts comprise according to the invention about 0.1% to 5% gold, preferably about 0.5% to 1.0% gold, particularly preferably 0.5% gold.

In a further preferred embodiment of the invention, a metal oxide-supported gold catalyst is employed according to the invention for selective oxidation of an oligosaccharide, of an oligosaccharide mixture or of a composition having a content thereof. A "metal oxide support" means a catalyst support which consists of at least one oxide of a main group or transition metal or metalloid, including compounds which comprise more than one metal and/or metalloid. Preference is given in this connection to oxides of metals or metalloids of main group 2 of the PTE such as MgO, CaO or BaO, oxides of metals or metalloids of main group 3 of the PTE such as $Al_2O_3$ or lanthanoid oxides or oxides of metals or metalloids of main group 4 of the PTE such as $SiO_2$, $TiO_2$, $SnO_2$ or $ZrO_2$. The compounds having more than one metal and/or metalloid are preferably silicates, especially aluminosilicates.

In a preferred embodiment, an $Al_2O_3$-supported gold catalyst is employed. The $Al_2O_3$-supported gold catalyst comprises according to the invention about 0.1% to 5% gold, preferably about 0.5% to 1% gold, particularly preferably 0.5% gold.

In a preferred embodiment, a $TiO_2$-supported gold catalyst is employed. The $TiO_2$-supported gold catalyst comprises according to the invention about 0.1% to 5% gold, preferably about 0.5% to 1% gold.

The metal oxide-supported gold catalysts used according to the invention for oligosaccharide oxidation can be prepared in particular by employing precipitation methods where the gold particles are deposited on the metal oxide support by precipitation or are precipitated together with a precursor of the metal oxide support. Precipitation methods, deposition-precipitation methods and methods for chemical deposition from the gas phase (CVD methods) are particularly suitable.

The carbon- or metal oxide-supported gold catalyst used for selective oligosaccharide oxidation is employed according to the invention in liquid phase, with the catalyst being in the form of a solid, whereas the oligosaccharides are present in liquid phase. The dioxygen employed for the oxidation is bubbled as gas through the liquid phase and dissolved in the liquid phase by vigorous agitation. The carbon- or metal oxide-supported gold catalyst is preferably employed in the form of a powder or granules.

"Oligosaccharides" mean in connection with the present invention compounds obtained by combining from 2 to 10 monosaccharide molecules with elimination of water, and which are glycosides or ethers. The term "oligosaccharide" also includes derivatives of an oligosaccharide which are formed from an oligosaccharide in one or more reaction steps. The oligosaccharides to be oxidized are particularly preferably according to the invention disaccharides, trisaccharides etc. The oligosaccharides to be oxidized comprise at their C1 carbon atom an oxidizable aldehyde group which is converted by the oxidation into a carboxy group. On the other hand, alcohol groups of the oligosaccharides are not oxidized.

The oligosaccharides employed according to the invention may be oligosaccharide aldoses having on the C1 carbon an oxidizable aldehyde group, or oligosaccharides in the 2-ketose form, where an oxidizable aldehyde function can be introduced at the C1 carbon atom.

In connection with the present invention, an "oligosaccharide aldose" means an oligosaccharide which has an aldehyde group (—CHO) on the C1 carbon. The selective oxidation of the aldehyde group of an oligosaccharide aldose results in an oligosaccharide aldonic acid. An "oligosaccharide aldonic acid" means an oligosaccharide acid obtained by oxidizing an aldehyde group of an oligosaccharide to the carboxy group.

The present invention therefore relates to a method for preparing an oligosaccharide aldonic acid or a mixture of various oligosaccharide aldonic acids by selective oxidation of one or more oligosaccharide aldoses having an oxidizable aldehyde group by use of a carbon- or metal oxide-supported gold catalyst.

A "2-ketose" means an oligosaccharide that has a keto group located in position 2. Oligosaccharides in the 2-ketose form can be converted into oligosaccharide aldoses, in which case the 2-ketose is initially converted into the enol form which is then tautomerized to the oxidizable oligosaccharide aldose.

The present invention therefore also relates to a method for preparing an oligosaccharide aldonic acid or a mixture of various oligosaccharide aldonic acids by use of one or more oligosaccharides in the 2-ketose form, where the 2-ketose(s) are initially converted into the tautomeric oligosaccharide aldose form(s) having an oxidizable aldehyde; group, which is/are then selectively oxidized by use of a carbon- or metal oxide-supported gold catalyst.

In connection with the present invention, an "oligosaccharide mixture" means a mixture of two or more chemically different oligosaccharides. The oligosaccharide mixture to be oxidized comprises in a preferred embodiment no other constituents apart from oligosaccharides. The oligosaccharide mixture to be oxidized may be either a homogeneous mixture or a heterogeneous mixture. If the oligosaccharide mixture to be oxidized is not in liquid form, or if the oligosaccharide mixture to be oxidized comprises a solid phase, the mixture is converted into the liquid phase, for example by preparing an aqueous solution, before the selective oxidation.

One embodiment of the invention relates to the use of an oligosaccharide mixture to be oxidized as initial substrate, in which at least one oligosaccharide constituent comprises a C1 carbon atom having an oxidizable aldehyde group, or in which the C1 carbon atom of at least one oligosaccharide constituent can be provided with an oxidizable aldehyde function before the selective oxidation.

A further preferred embodiment of the invention relates to the use of an oligosaccharide mixture to be oxidized as starting substrate, where the mixture to be oxidized preferably comprises a plurality of oligosaccharides which either already have an oxidizable aldehyde group at their C1 carbon, or an oxidizable aldehyde group can be introduced at their C1 carbon atom before the selective oxidation. In this embodiment, the oligosaccharide to be oxidized may therefore include a plurality of different oligosaccharide aldoses and/or oligosaccharides in 2-ketose form. The oligosaccharide mixture to be oxidized particularly preferably consists exclusively of individual oligosaccharide components which either already have an oxidizable aldehyde group at their C1 carbon, or an oxidizable aldehyde group can be introduced at their C1 carbon atom before the selective oxidation. In this embodiment, the oligosaccharide to be oxidized thus consists exclusively of different oligosaccharide aldoses and/or oligosaccharides in 2-ketose form.

In connection with the present invention, a "composition comprising at least one oligosaccharide or an oligosaccharide mixture" means a mixture of different chemical compounds, where at least one constituent of the composition is an oligosaccharide whose C1 carbon atom has a free aldehyde group, or can be provided with an oxidizable aldehyde group before the selective oxidation. The other constituents of the composition to be oxidized may be for example other carbohydrates, for example nonoxidizable or selectively oxidizable monosaccharides, proteins, pectins, acids, fats, salts, flavorings etc. The composition to be oxidized may, of course, comprise a plurality of different oligosaccharide aldoses and/or oligosaccharides in 2-ketose form.

In a particularly preferred embodiment, the oligosaccharide to be oxidized is a disaccharide. The disaccharide to be oxidized may be a disaccharide aldose such as maltose, lactose, cellobiose or isomaltose. Selective oxidation of maltose according to the invention with use of the method of the invention results in maltobionic acid as oxidation product. Lactose oxidation using the method of the invention results in lactobionic acid as oxidation product.

In a further particularly preferred embodiment of the invention, a disaccharide ketose is employed as oligosaccharide to be oxidized. The disaccharide ketose to be oxidized is preferably palatinose. Before the oxidation, palatinose is converted according to the invention into the tautomeric aldose form, which is then oxidized.

In a further particularly preferred embodiment of the invention, the oligosaccharide mixture to be oxidized or the oligosaccharide-containing composition to be oxidized is a maltodextrin. Selective oxidation of maltodextrin using the method of the invention results in an oxidation product which has according to the invention a proportion of maltobionic acid and gluconic acid.

In a further particularly preferred embodiment, the oligosaccharide-containing composition to be oxidized is a starch syrup.

In a preferred embodiment of the method of the invention for selective carbohydrate oxidation, an aqueous solution of the oligosaccharide or oligosaccharide mixture to be oxidized or of a composition having a content thereof is prepared and comprises the oligosaccharide or the oligosaccharide mixture in an amount of at least about 10 mmol/l, preferably at least about 100 mmol/l, 150 mmol/l, 200 mmol/l or 250 mmol/l and most preferably at least about 1000 mmol/l or 1500 mmol/l. Subsequently, the carbon- or metal oxide-supported gold catalyst, preferably in powder form, is added in an amount of about 100 mg/l to 10 g/l to the aqueous oligosaccharide solution, preferably employing about 1 g of catalyst per liter. The ratio between the amount of the oligosaccharide(s) to be oxidized or of the oligosaccharide mixture and the amount of the gold present on the metal oxide support or carbon support is according to the invention at least about 300, more preferably more than 350, 500, 1000, 1500, 2000, 2500, 3000, 3500 or 4000 and most preferably more than 9000, 10 000, 15 000, 20 000, 25 000, 30 000, 35 000 or 40 000.

In a preferred embodiment of the method of the invention for selective oligosaccharide oxidation, the selective oxidation of the at least one oligosaccharide, of the oligosaccharide mixture or of the composition having a content thereof is carried out at a pH of from 7 to 11, preferably 8 to 10. The temperature employed for carrying out the carbohydrate oxidation according to the invention is from 20° C. to about 140° C., preferably 40° C. to 90° C., particularly preferably 50° C. to 80° C. The pressure according to the invention is about 1 bar to about 25 bar. During the oxidation, according to the invention oxygen and/or air is bubbled through the aqueous solution of the oligosaccharide, of the mixture or of the composition at a gas input rate of from 100 ml/(min×$L_{reactor\ volume}$) to 10 000 ml/(min×$L_{reactor\ volume}$), preferably of 500 ml/(min×$L_{reactor\ volume}$).

The present invention likewise relates to the oxidation products which are prepared by use of the method of the invention and which are obtained either by selective oxidation of at least one carbohydrate, a carbohydrate mixture or a composition having a content thereof by use of a metal oxide-supported gold catalyst or by selective oxidation of at least one oligosaccharide, an oligosaccharide mixture or a composition having a content thereof by use of a carbon- or metal oxide-supported gold catalyst. The oxidation products prepared according to the invention may, depending on the starting material used, be either an aldonic acid, a mixture of different aldonic acids or a composition which, besides constituents such as fats, pectins, proteins, salts, flavorings etc., includes one or more aldonic acids. Especially when a single carbohydrate is employed as precursor, the oxidation products obtained according to the invention have a very high purity because of the exceptionally high selectivity of the gold catalysts used according to the invention. The oxidation products obtained according to the invention are also distinguished from conventional products by being free of microbial metabolic products which are possibly harmful to health.

In a preferred embodiment, the oxidation product is gluconic acid, which is obtainable by selective oxidation of glucose. The gluconic acid obtained according to the invention is notable for high purity, the proportion of gluconic acid in the overall oxidation product being more than 95%, preferably more than 97%, more preferably more than 98% and most preferably more than 99%.

The gluconic acid prepared by use of the method of the invention can, where appropriate after further purification steps using suitable methods such as chromatographic methods, be employed as addition to food products, beverages or animal feed, for cosmetic applications, pharmaceutical applications or as detergent, for example in cleaning compositions. Gluconic acid has for example outstanding properties as antioxidant. It is further known that gluconic acid is an outstanding agent for skin care.

The present invention therefore relates to the use of the gluconic acid prepared by use of the oxidation method of the invention as addition to food products or animal feeds and for producing pharmaceutical compositions, cosmetic compositions and detergents.

In a further preferred embodiment, the oxidation product is maltobionic acid, which is obtainable by selective oxidation of maltose. The maltobionic acid obtained according to the invention is notable for high purity, the proportion of maltobionic acid in the overall oxidation product being more than 95%, preferably more than 97%, more preferably more than 98% and most preferably more than 99%.

The maltobionic acid prepared by use of the method of the invention can, where appropriate after further purification steps, be employed as addition to food products, beverages or animal feed or for pharmaceutical applications. Maltobionic acid can, for example after purification by ion exchange chromatography, be converted into the lactone form and then condensed for example with 1,3-diamino-2-propanal, resulting in the bisamide of maltobionic acid. The bisamide of maltobionic acid can be employed as anticoagulant for oral administration and/or as antithrombolytic.

The present invention therefore relates to the use of the maltobionic acid prepared by use of the oxidation method of the invention as addition to food products or animal foods and for producing pharmaceutical compositions.

In a further preferred embodiment, the oxidation product obtained according to the invention is lactobionic acid, which is obtainable by oxidation of lactose. The lactobionic acid obtained according to the invention is notable for high purity, the proportion of lactobionic acid in the overall oxidation product being more than 95%, preferably more than 97, more preferably more than 98% and most preferably more than 99%.

The lactobionic acid prepared by use of the method of the invention can, where appropriate after further purification steps, be employed as addition to food products, beverages or animal feed and for cosmetic applications and pharmaceutical applications. Because of its hygroscopic properties, lactobionic acid is able to bind atmospheric water, so that lactobionic acid forms a natural gel matrix. The gel matrix formed in this way comprises about 14% water. Owing to its ability to form such a gel matrix, lactobionic acid is, like gluconic acid, an outstanding agent for skin care. Lactobionic acid additionally has outstanding properties for forming metal chelates and can therefore be employed for preparing a transplantation solution, for example the Wisconsin transplantation solution, which is used for transporting and storing organs to be transplanted. Lactobionic acid can also be employed as cobuilder in washing powder, in which case the washing powder may comprise up to 40% lactobionic acid. Since lactobionic acid has a mild sweet-sour taste, it can likewise be employed for manufacturing food products and animal feed.

The present invention therefore relates to the use of the lactobionic acid prepared by use of the oxidation method of the invention for the manufacture of food products, animal feed, cosmetic compositions, pharmaceutical products and washing powder.

In a further preferred embodiment, the oxidation product obtained according to the invention is a product mixture which comprises a high proportion of gluconic acid and maltobionic acid and can be obtained by oxidation of maltodextrin.

The maltobionic acid- and gluconic acid-containing oxidation product obtained by selective maltodextrin oxidation can, where appropriate after further purification steps, be employed in particular for further enrichment of maltobionic acid and gluconic acid, especially for the manufacture of food products and pharmaceutical compositions.

The present invention therefore also relates to the use of the maltodextrin oxidation product obtained by use of the oxidation method of the invention for the manufacture of food products, pharmaceutical products and cosmetic compositions.

In a further preferred embodiment, the oxidation product obtained according to the invention is a product that has a high proportion of maltobionic acid and can be obtained by selective oxidation of a starch syrup. The oxidation product obtained on oxidation of starch syrup can be employed in particular for the manufacture of food products and animal feed.

The present invention likewise relates to the use of a gold catalyst comprising nanodispersed gold particles on a metal oxide support for selective oxidation of at least one carbohydrate, a carbohydrate mixture or a composition having a content thereof. The catalyst for selective oxidation of a carbohydrate, the mixture or a composition containing them is preferably according to the invention a gold catalyst whose support is a $TiO_2$ support. The gold catalyst with the $TiO_2$ support which is used according to the invention comprises about 0.1% to 5% gold, preferably about 0.5% to 1% gold, particularly preferably 0.5% gold. In a further preferred embodiment, the gold catalyst used according to the invention includes an $Al_2O_3$ support. The gold catalyst with the $Al_2O_3$ support used according to the invention comprises about 0.1% to 5% gold, preferably about 0.5% to 1% gold. The carbohydrate to be oxidized may be either a carbohydrate aldose or a carbohydrate in 2-ketose form. The carbohydrate to be oxidized may be a monosaccharide, an oligosaccharide, a mixture thereof or a composition having a content thereof. If the monosaccharide to be oxidized is glucose, gluconic acid is obtained as glucose oxidation product on use of the gold catalyst. If the oligosaccharide to be oxidized is a disaccharide aldose such as maltose, maltobionic acid is obtained as oxidation product. If the oligosaccharide to be oxidized is a disaccharide aldose such as lactose, lactobionic acid is obtained as oxidation product. In further embodiments, the gold catalyst employed according to the invention can be employed for the oxidation of maltodextrin or for oxidation of a starch syrup.

The present invention therefore also relates to the use of a metal oxide-supported gold catalyst for preparing one or more aldonic acid(s) from one or more carbohydrate aldose(s). The present invention also relates to the use of a metal oxide-supported gold catalyst for preparing one or more aldonic acid(s) from one or more carbohydrate(s) in 2-ketose form, where the carbohydrate(s) in 2-ketose form is/are initially converted into the tautomeric aldose form(s) before the oxidation, and then selectively oxidized.

The present invention also relates to the use of a carbon-supported gold catalyst for selective oxidation of an oligosaccharide, of an oligosaccharide mixture or of a composition having a content thereof, where the oligosaccharide(s) is oxidized to the corresponding oligosaccharide aldonic acid(s). The carbon-supported gold catalyst used according to the invention comprises about 0.1% to 5% gold, preferably about 0.5% to 1% gold, particularly preferably 0.5% gold. It is possible to employ as oligosaccharide to be oxidized either an oligosaccharide aldose or an oligosaccharide in 2-ketose form, with the oligosaccharide in 2-ketose form being initially converted into the tautomeric oligosaccharide aldose form and then oxidized.

The present invention therefore also relates to the use of a carbon-supported gold catalyst for preparing one or more oligosaccharide aldonic acid(s) from one or more oligosaccharide aldose(s). The present invention also relates to the use of a carbon-supported gold catalyst for preparing one or more oligosaccharide aldonic acid(s) from one or more oligosaccharide(s) in 2-ketose form, with the oligosaccharide(s) in 2-ketose form being initially converted into the tautomeric aldose form(s) before the oxidation, and then selectively oxidized.

The present invention is explained in more detail by means of the following figures and examples. The figures show:

EXAMPLES

The following examples are provided only for the purpose of illustrating the invention and are not intended to be limiting in any manner.

Reference Example

Glucose Oxidation with Platinum and Palladium Catalysts

The catalysts employed were a 5% platinum- and 5% bismuth-containing carbon-supported catalyst (supplied by Degussa), a 5% platinum-containing catalyst on an Al$_2$O$_3$ support (supplied by Engelhard) and a 5% palladium-containing catalyst on an Al$_2$O$_3$ support. Oxidation of glucose took place under the following reaction conditions:

| | |
|---|---|
| Reaction volume (batch): | 500 ml |
| Amount of catalyst: | 1 g/l |
| Initial substrate concentration: | 100 mmol/l |
| pH: | 11 |
| Temperature: | 40° C. |
| Pressure: | 1 bar |
| O$_2$ gas input rate: | 500 ml/min |
| Stirring speed: | 700 rpm |

The results obtained with use of the catalysts detailed above in the oxidation of glucose are shown in Table 1 below.

TABLE 1

Comparison of Pt and Pd catalysts in relation to oxidation of glucose, initial activity up to 10% conversion and formation of fructose by isomerization

| Property | Pt (5%) Bi (5%)/C | 5% Pt/Al$_2$O$_3$ | 5% Pd/Al$_2$O$_3$ |
|---|---|---|---|
| Glucose conversion in %* | >95 | >95 | 90 |
| Initial activity in mmol$_{glucose}$/(g$_{metal}$ · min) | 19 | 62 | 76 |
| Selectivity for gluconic acid in % | 85 | 83 | 92 |
| Selectivity for other oxidation products in %** | 11 | 12 | 4 |
| Selectivity for fructose in % | 2.5 | 2.5 | <0.5 |

Figure 1:
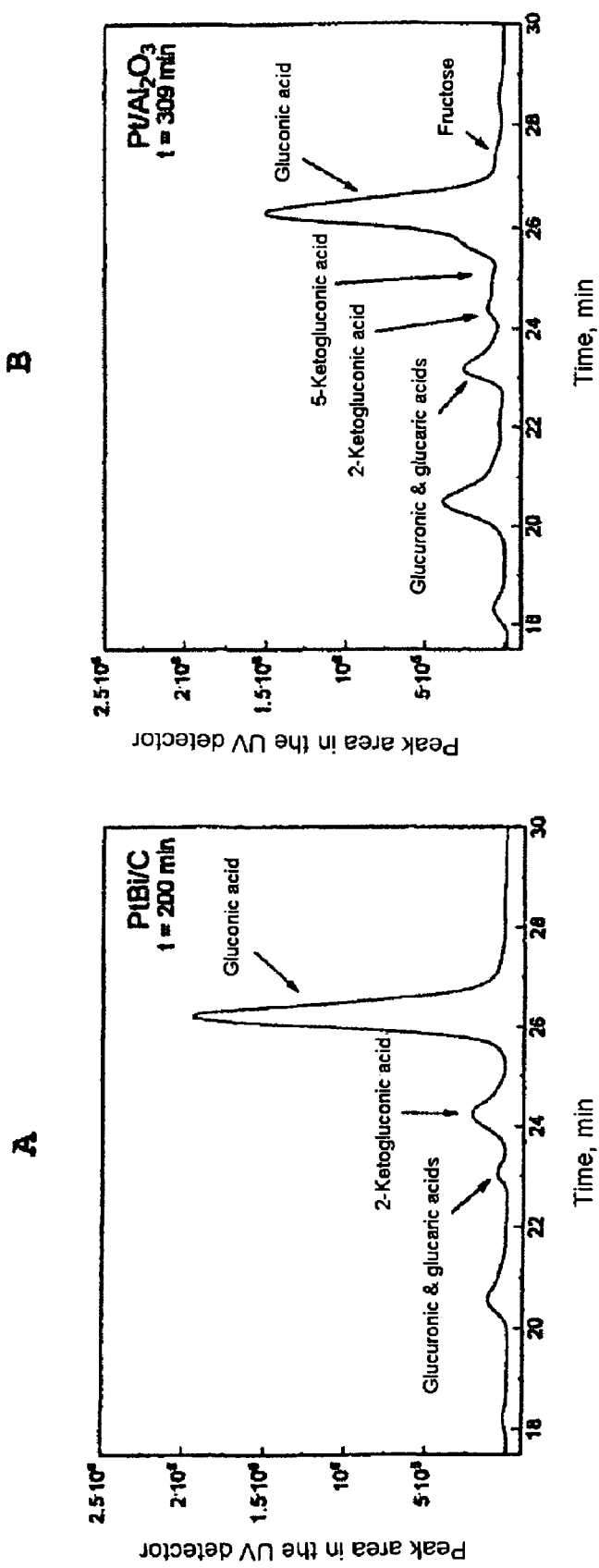
FIG. 1 shows chromatograms, obtained with the aid of a UV detector, of the product mixtures obtained on catalytic oxidation of glucose with use of platinum and palladium catalysts. A: Pt—Bi/C catalyst; B: Pt/Al$_2$O$_3$ catalyst.

*conversion at which the reaction was stopped
**other oxidation products: glucuronic acid, 2- and 5-ketogluconic acid, and glucaric acid Table 1 shows that conventional platinum and palladium catalysts show only moderate selectivity in relation to the formation of gluconic acid on oxidation of glucose, and that considerable amounts of other oxidation products such as glucuronic acid, glucaric acid, 2-ketogluconic acid and 5-ketogluconic acid are formed. This range of products is also evident in FIG. 1, which shows product chromatograms obtained with the aid of a UV detector. It is evident from the results obtained that the platinum or palladium catalysts conventionally used are unsuitable for selective preparation of gluconic acid by oxidation of glucose.

Example 1

Oxidation of Glucose with Use of Gold Catalysts

The following types of catalyst were employed for this example:
A: 1% Au/C type 138 (ACA)
B: 0.95% Au/Al$_2$O$_3$ (ACA)
C: 0.7% Au/C type 11 (ACA)
D: 1% Au/TiO$_2$ type 5 (ACA)
E: 0.5% Au/TiO$_2$ type 102 (ACA)
F: 0.5% Au/TiO$_2$ type 149 (ACA)

The oxidation of glucose took place under the following reaction conditions:

| | |
|---|---|
| Reaction volume (batch): | 500 ml |
| Amount of catalyst: | 1 g/l |
| Initial substrate concentration: | 100 mmol/l |
| pH: | 11 |
| Temperature: | 40° C. |
| Pressure: | 1 bar |
| O$_2$ gas input rate: | 500 ml/min |
| Stirring speed: | 700 rpm |

The results obtained on oxidation of glucose with use of the catalysts detailed above are shown in Table 2.

TABLE 2

Comparison of various gold catalysts in relation to selectivity of oxidation of glucose, initial activity up to 10% conversion and fructose formation as a result of isomerization

| Property | A | B | C | D | E | F |
|---|---|---|---|---|---|---|
| Glucose conversion in %* | 93 | 97 | 88 | 74 | 95 | 100 |
| Initial activity in mmol$_{glucose}$/g$_{metal}$ · min | 156 | 133 | 390 | 105 | 371 | 550 |
| Selectivity for gluconic acid in % | 95 | 95 | 97 | 95 | 98 | 98 |

TABLE 2-continued

Comparison of various gold catalysts in relation to selectivity of oxidation of glucose, initial activity up to 10% conversion and fructose formation as a result of isomerization

| Property | A | B | C | D | E | F |
|---|---|---|---|---|---|---|
| Selectivity for other oxidation products in %** | 0 | <2 | <1 | 0 | 0 | <1 |
| Selectivity for fructose in % | 5 | 3 | 2 | 5 | 1 | 1 |

*conversion at which the reaction was stopped
**other oxidation products: glucuronic acid, 2- and 5-ketogluconic acid, and glucaric acid It is evident from Table 2 that the gold catalysts employed have an activity in relation to the oxidation of glucose which is at least one order of magnitude or even higher than the activity of the platinum and palladium catalysts used in the comparative example.

Figure 2:
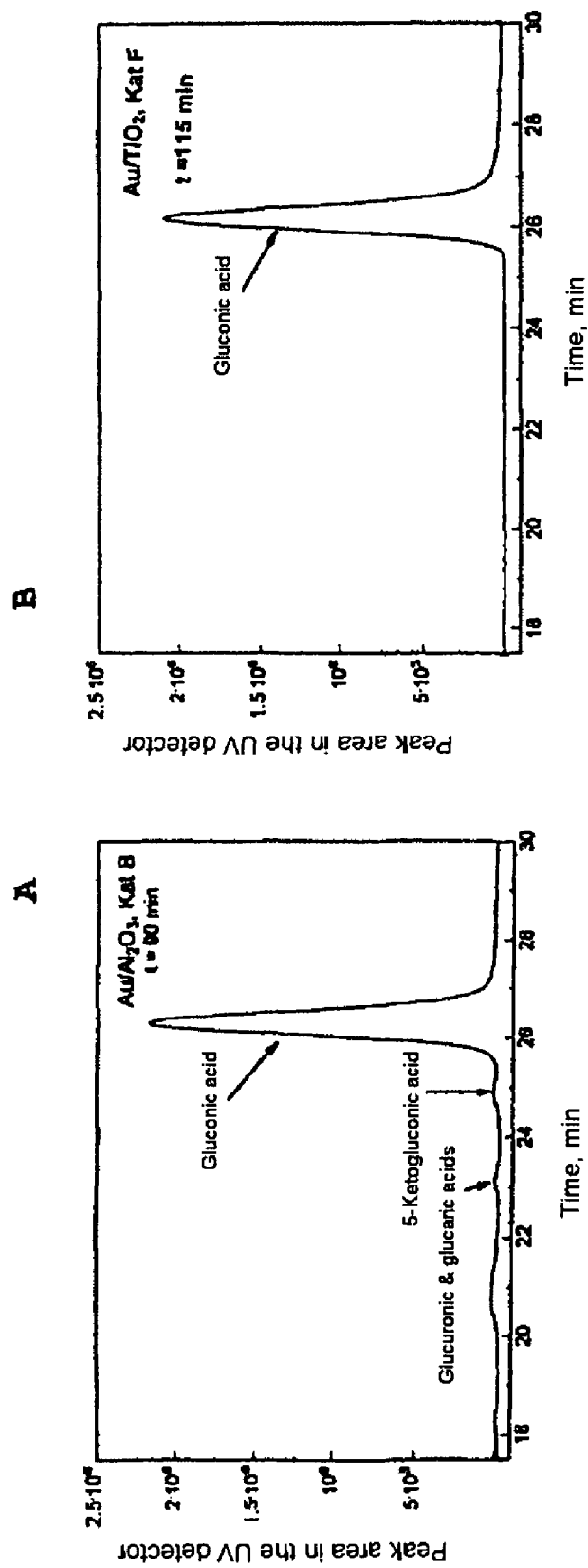
FIG. 2 shows chromatograms, obtained with the aid of a UV detector, of the products obtained according to the invention on catalytic oxidation of glucose with use of gold catalysts. A: 0.95% Au/Al$_2$O$_3$ catalyst; B: 0.5% Au/TiO$_2$ catalyst.

Table 2 additionally shows the exceptionally high selectivity of the gold catalysts used for the formation of gluconic acid from glucose. The high selectivity of the employed gold catalysts in relation to the preparation of gluconic acid is also evident in FIG. 2. On use of the Au/TiO₂ catalyst (catalyst F) (FIG. 2B), only gluconic acid is formed, while other oxidation products are undetectable. By contrast, on use of the Au/Al₂O₃ catalyst (catalyst B) there is formation not only of gluconic acid but also of small amounts of other oxidation products such as glucuronic acid, glucaric acid and 5-ketogluconic acid. The amount of these oxidation products is, however, distinctly lower by comparison with the amounts of these oxidation products obtained on use of platinum or palladium catalysts.

It was also found with the gold catalysts employed according to the invention that they lead to only very slight isomerization of fructose, but the fructose itself is not further oxidized.

It is evident from the results obtained that the gold catalysts employed according to the invention are considerably more suitable for preparing gluconic acid from glucose than the platinum- or palladium-based catalysts used in the comparative example.

Example 2

Oxidation of Glucose with Au/TiO₂ Catalysts

The 0.5% Au-containing catalyst with TiO₂ support (catalyst G) prepared in Example 1 was selected for further investigations where the oxidation of glucose was tested under varying reaction conditions.

Unless indicated otherwise, the same reaction conditions as stated in Example 1 were employed.

Influence of the pH on the Oxidation of Glucose

The results of the oxidation of glucose on use of the 0.5% Au/TiO₂ catalyst (catalyst G) at different pH values are shown in Table 3.

TABLE 3

Oxidation of glucose with a 0.5% Au/TiO₂ catalyst at various pH values, initial activity up to 10% conversion, formation of fructose as a result of isomerization

| Property | pH 7 | pH 9 | pH 11 |
|---|---|---|---|
| Glucose conversion in %* | 80 | 100 | 100 |
| Initial activity in $mmol_{glucose}/(g_{metal} \cdot min)$ | 194 | 416 | 550 |
| Selectivity for gluconic acid in % | >99 | >99.5 | 98 |
| Selectivity for other oxidation products in %** | <0.5 | 0 | <0.5 |
| Selectivity for fructose in % | 0 | 0 | 1 |

*conversion at which the reaction was stopped
**other oxidation products: glucuronic acid, 2- and 5-ketogluconic acid, and glucaric acid It is evident from Table 3 that the activity of the Au/TiO₂ catalyst is somewhat lower in the only weakly alkaline to neutral pH range, whereas the selectivity increases further.

Influence of the Temperature on the Oxidation of Glucose

The results of the oxidation of glucose using the Au/TiO₂ catalyst at different temperatures, at a pH of 9 and with an initial glucose concentration of 250 mmol/l are shown in Table 4.

TABLE 4

Oxidation of glucose with a 0.5% Au/TiO₂ catalyst at various temperatures, with an initial glucose concentration of 250 mmol/l and at a pH of 9, initial activity to 10% conversion, formation of fructose as a result of isomerization

| Property | 40° C. | 50° C. | 70° C. |
|---|---|---|---|
| Glucose conversion in %* | 95 | 100 | 100 |
| Initial activity in $mmol_{glucose}/(g_{metal} \cdot min)$ | 320 | 1056 | 1404 |
| Selectivity for gluconic acid in % | >99.5 | >99 | 95.5 |
| Selectivity for other oxidation products in %** | <0.1 | <0.1 | <0.2 |
| Selectivity for fructose in % | 0 | <0.5 | 3 |

*conversion at which the reaction was stopped
**other oxidation products: glucuronic acid, 2- and 5-ketogluconic acid, and glucaric acid It is evident from Table 4 that the selectivity of the oxidation of glucose declines somewhat as the reaction temperature increases. However, this is attributable not to the formation of oxidation products other than gluconic acid, but almost exclusively to the increased formation of fructose in accordance with a higher rate of isomerization of glucose to fructose.

Influence of the Initial Glucose Concentration on the Oxidation of Glucose

The influence of the initial glucose concentration on the oxidation of glucose using the 0.5% Au/TiO₂ catalyst at a temperature of 40° C. and a pH of 9 is shown in Table 5.

TABLE 5

Oxidation of glucose with a 0.5% Au/TiO$_2$ catalyst with various initial glucose concentrations and at a pH of 9, initial activity up to 10% conversion, formation of fructose as a result of isomerization

| Property | 10 mmol/l | 250 mmol/l | 1100 mmol/l |
|---|---|---|---|
| Glucose conversion in %* | 40 | 95 | 100 |
| Initial activity in mmol$_{glucose}$/(g$_{metal}$ · min) | 20 | 320 | 1200 |
| Selectivity for gluconic acid in % | 99.4 | 99.6 | 99.2 |
| Selectivity for other oxidation products in %** | 0 | 0 | 0 |
| Selectivity for fructose in % | 0.6 | <0.1 | 0.4 |

*conversion at which the reaction was stopped
**other oxidation products: glucuronic acid, 2- and 5-ketogluconic acid, and glucaric acid It is evident from the results shown in Table 5 that the gold catalyst used also shows excellent activity and selectivity in concentrated glucose solutions (1100 mmol/l; about 20% glucose/l), with distinctly more glucose being converted in the same reaction time.

Example 3

Long-Term Stability of the Au/TiO$_2$ Catalyst in the Oxidation of Glucose

The long-term stability of the 0.5% Au/TiO$_2$ catalyst (cat G in Example 1) was tested in the form of repeated batch tests. For this purpose, a glucose oxidation was carried out throughout the day. Overnight or over the weekend, the catalyst was left in the reaction solution which consists principally of an aqueous gluconic acid solution, so that the catalyst was able to sediment. The next day, the supernatant was decanted off, and the reactor was charged with fresh glucose solution, and the next glucose oxidation was carried out. In total, 17 batch tests were carried out at a pH of 9, at a temperature of 40° C. and with an initial glucose concentration of 250 mmol/l (equivalent to about 4.5% glucose/l). The further reaction conditions were as described in Example 1. The results for some selected batch tests are listed in Table 6.

TABLE 6

Long-term test on the oxidation of glucose with a 0.5% Au/TiO$_2$ catalyst with an initial glucose concentration of 250 mmol/l, at a temperature of 40° C. and at a pH of 9, initial activity up to 10% conversion, formation of fructose as a result of isomerization

| Property | Batch number | | | | |
|---|---|---|---|---|---|
| | 1 | 5 | 10 | 15 | 17 |
| Glucose conversion in %* | 95 | 97 | 99 | 94 | 56 |
| Initial activity in mmol$_{glucose}$/(g$_{metal}$ · min) | 320 | 350 | 460 | 430 | 570 |
| Selectivity for gluconic acid in % | 99.5 | 99.7 | 99.6 | 99 | 99.3 |
| Selectivity for other oxidation products in %** | <0.1 | <0.1 | <0.1 | <0.1 | <0.1 |
| Selectivity for fructose in % | <0.1 | <0.1 | 0.1 | 0.3 | <0.3 |

*conversion at which the reaction was stopped
**other oxidation products: glucuronic acid, 2- and 5-ketogluconic acid, and glucaric acid The results shown in Table 6 show that the catalytic properties of the gold catalyst can be regarded as constant over at least the investigated test period, and thus the catalyst has an extremely long useful life. In total, about 360 g of glucose were virtually 100% converted into gluconic acids in these tests with 0.5 g of the 0.5% Au/TiO$_2$ catalyst. This corresponds to about 145 t of glucose/kg of gold. Because of the catalyst loss which is not taken into account in this calculation and which results from the taking of samples during the tests, this value is probably even distinctly higher. It must also be taken into account in this connection that the catalyst is presumably stable for much longer than the investigated period, and thus this value may increase again correspondingly.

Example 4

Selective Oxidation of Lactose with Gold Catalysts

Lactose is a 1,4 linked disaccharide which consists of a glucose moiety and a galactose moiety. The 0.5% Au/TiO$_2$ (catalyst G) was employed to oxidize lactose. For comparison, the 5% Pt/Al$_2$O$_3$ catalyst (Engelhard) and the 5% Pd/Al$_2$O$_3$ catalyst were also employed. The oxidation of lactose took place under the following reaction conditions:

| | |
|---|---|
| Reaction volume (batch): | 500 ml |
| Amount of catalyst: | 1 g/l |
| Initial substrate concentration: | 10 mmol/l |
| pH: | 8 |
| Temperature: | 80° C. |
| Pressure: | 1 bar |
| O$_2$ gas input rate: | 500 ml/min |
| Stirring speed: | 700 rpm |

Table 7 shows the results of the catalytic oxidation of lactose obtained with use of the various catalysts.

TABLE 7

Use of various catalysts for oxidation of lactose, initial activity up to 10% conversion

| Property | 5% Pt/Al$_2$O$_3$ | 5% Pd/Al$_2$O$_3$ | 0.5% Au/TiO$_2$ |
|---|---|---|---|
| Conversion after 20 min in %* | <40 | <60 | >95 |
| Initial activity in mmol$_{substrate}$/g$_{metal}$ · min)* | 7.1 | 16.4 | 143 |

*estimated from titration curve

Figure 3:
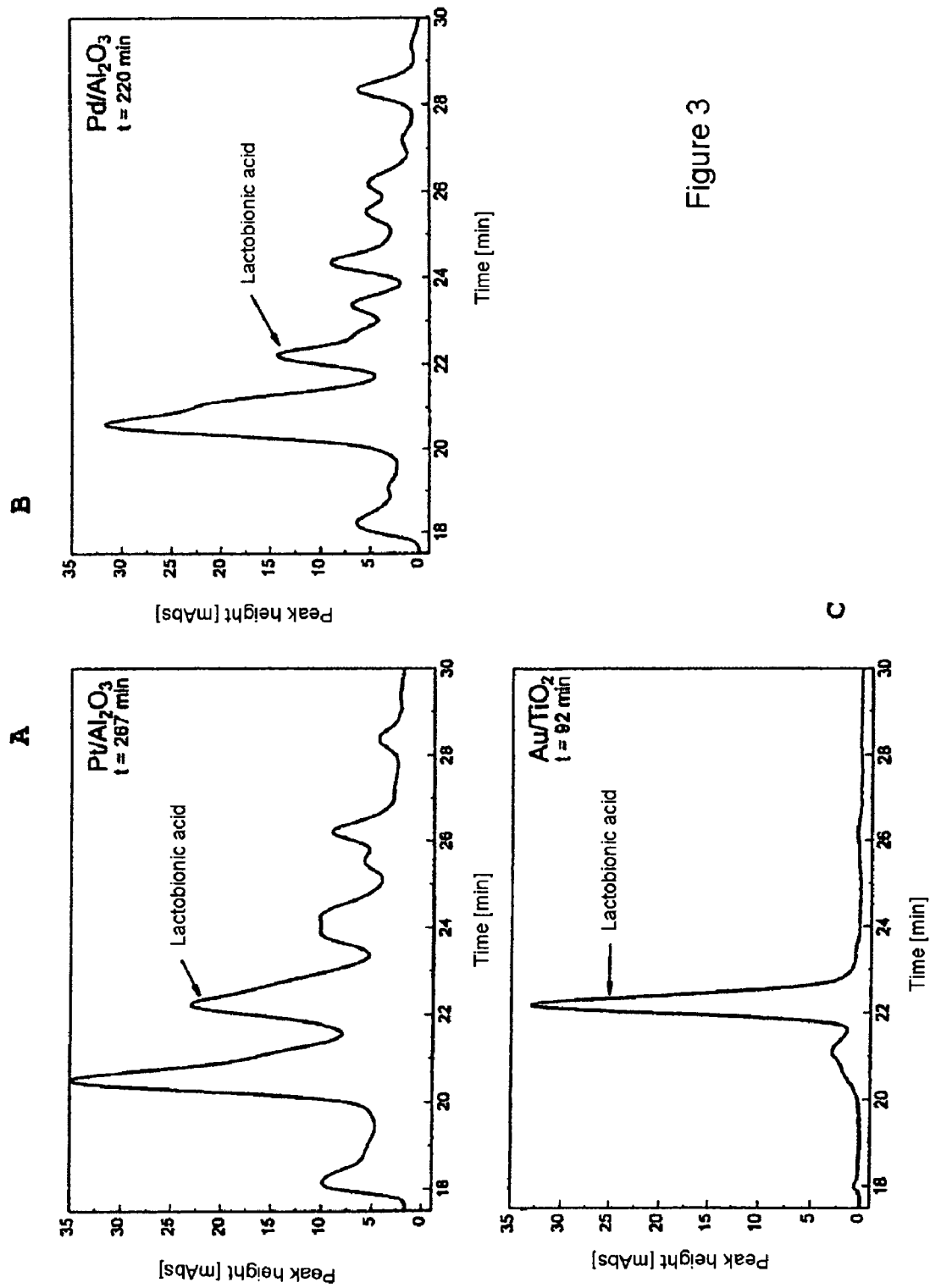
FIG. 3 shows chromatograms, obtained with the aid of a UV detector, of the products obtained on catalytic oxidation of lactose with use of platinum, palladium and gold catalysts. A: Pt/Al$_2$O$_3$ catalyst; B: Pd/Al$_2$O$_3$ catalyst; C: 0.5% Au/TiO$_2$ catalyst.

Because of analytical problems it is possible to indicate the selectivity of the individual catalysts for oxidation of lactose only qualitatively. It is possible to use for this purpose the chromatograms which were obtained in the UV detector and are shown in FIG. 3 and which show the oxidized reaction products. It is evident from FIG. 3 that the $TiO_2$-supported gold catalyst employed according to the invention has an extremely high selectivity in relation to the preparation of lactobionic acid, with virtually no other oxidation products being detectable. In contrast thereto, oxidation of lactose in the presence of the platinum or palladium catalyst leads to a mixture of different products, and lactobionic acid is not the main product.

Example 5

Selective Oxidation of Maltose Using Gold Catalysts

Maltose is a 1,4-linked disaccharide which consists of two glucose units. Moreover, one glucose moiety has an aldehydic C1 carbon. Each of the two glucose units of maltose comprise an alcoholic C6 carbon atom. Oxidation of maltose was carried out using the 0.5% $Au/TiO_2$ catalyst (catalyst G). For comparison, maltose was also oxidized using the 5% $Pt/Al_2O_3$ catalyst (Engelhard) and the 5% $Pd/Al_2O_3$ catalyst. Oxidation of maltose took place under the following reaction conditions:

| | |
|---|---|
| Reaction volume (batch): | 500 ml |
| Amount of catalyst: | 1 g/l |
| Initial substrate concentration: | 10 mmol/l |
| pH: | 8 |
| Temperature: | 80° C. |
| Pressure: | 1 bar |
| $O_2$ gas input rate: | 500 ml/min |
| Stirring speed: | 700 rpm |

Table 8 shows the results obtained in the oxidation of maltose.

TABLE 8

Use of different catalysts for oxidation of maltose, initial activity up to 10% conversion

| Property | 5% $Pt/Al_2O_3$ | 5% $Pd/Al_2O_3$ | 0.5% $Au/TiO_2$ |
|---|---|---|---|
| Conversion after 20 min in %* | <80 | 100 | 100 |
| Initial activity in $mmol_{substrate}/g_{metal} \cdot min)^*$ | 12.3 | 22.2 | 110 |

*estimated from titration curve

Figure 4:
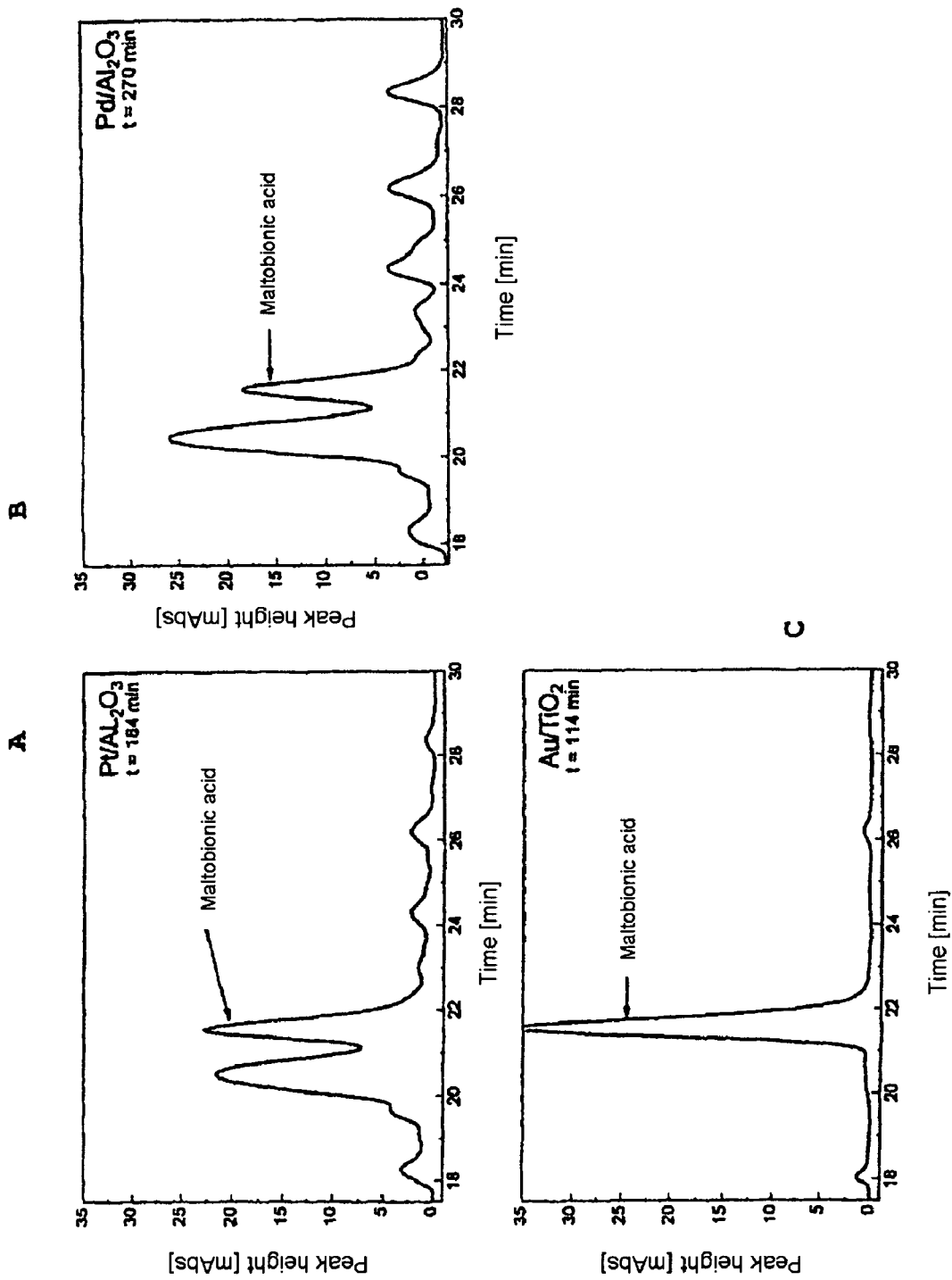
FIG. 4 shows chromatograms, obtained with the aid of a UV detector, of the products obtained on catalytic oxidation of maltose with use of platinum, palladium and gold catalysts. A: Pt/Al$_2$O$_3$ catalyst; B: Pd/Al$_2$O$_3$ catalyst; C: 0.5% Au/TiO$_2$ catalyst.

Because of analytical problems, the selectivity in relation to the oxidation of maltose to maltobionic acid can be indicated only qualitatively. It is possible to use for this purpose the product chromatograms in the UV detector which are shown in FIG. 4 and on the basis of which the oxidized reaction products are detectable. FIG. 4 shows chromatograms of the products obtained on use of the indicated catalysts in the oxidation of maltose. It is evident from FIG. 4 that the gold catalyst used has a considerably higher selectivity in relation to the preparation of maltobionic acid by comprison with the platinum and palladium catalysts, with virtually no other oxidation products being detectable. By contrast, other oxidation products are also formed with high selectivity with the platinum or palladium catalyst. These results show that the $Au/TiO_2$ catalyst used shows a selectivity in the oxidation of maltose which is just as high as for the oxidation of lactose.

Example 6

Oxidation of Maltodextrin Using a Gold Catalyst

Maltodextrins are mixtures of oligosaccharides which result from the linkage of glucose units by a 1,4-glycosidic bond. Agenamalt 20.222 (maltodextrin DE 19) was used for the example. According to the manufacturer's information, the maltodextrin DE 19 used has the following composition:

| | |
|---|---|
| Glucose: | 3.5-4.5% in DM |
| Maltose: | 3.5-4.5% in DM |
| Maltotriose: | 4.5-5.5% in DM |
| Oligosaccharides: | remainder |

The 5% $Pt/Al_2O_3$ catalyst (Engelhard), the 5% $Pd/Al_2O_3$ catalyst and the 0.5% $Au/TiO_2$ catalyst (catalyst G) were employed for the oxidation of maltodextrin. The oxidation of maltodextrin took place under the following reaction conditions:

| | |
|---|---|
| Reaction volume (batch): | 500 ml |
| Amount of catalyst: | 1 g/l |
| Initial substrate concentration: | 10 mmol/l |
| pH: | 8 |
| Temperature: | 80° C. |
| Pressure: | 1 bar |
| $O_2$ gas input rate: | 500 ml/min |
| Stirring speed: | 700 rpm |

Figure 5:
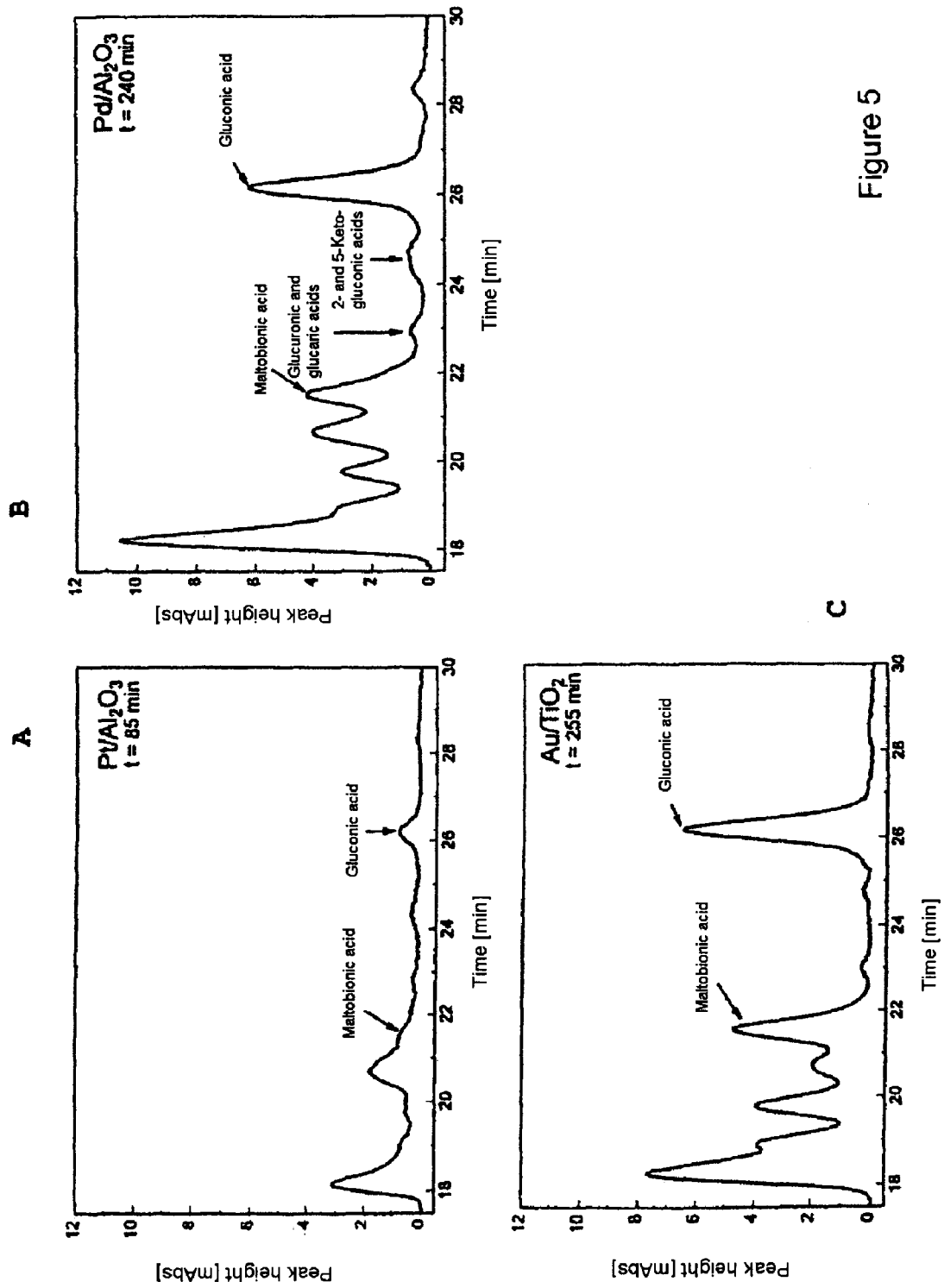
FIG. 5 shows chromatograms, obtained with the aid of a UV detector, of the products obtained on catalytic oxidation of maltodextrin with use of platinum, palladium and gold catalysts. A: Pt/Al$_2$O$_3$ catalyst; B: Pd/Al$_2$O$_3$ catalyst; C: 0.5% Au/TiO$_2$ catalyst.

Because of serious analytical problems, it is not possible to indicate either the conversion or the activity for the individual catalyst types. Nevertheless, an oxidation reaction proceeds with each of the catalysts investigated. FIG. 5 shows a qualitative comparison of the individual UV chromatograms for the products on termination of the reaction.

It is evident from FIG. 5 that a considerable oxidation proceeds in particular with the Pd catalyst and the Au catalyst employed according to the invention, which is also supported by the amount of titrated KOH (Pt: 0.7 ml; Pd: 2.8 ml; Au: 2.2 ml each at t=85 min). Comparison of the product mixture obtained using the Pd catalyst with the product mixture obtained using the Au catalyst shows a noteworthy difference. The substance with the retention time of 20.2 min is formed with distinctly higher selectivity by the Pd catalyst than is the case with the Au catalyst. The identity of this substance is, however, unknown. By contrast, the gold catalyst of the invention shows a distinctly higher selectivity for gluconic acid and maltobionic acid than the Pd catalyst.

Example 7

Preparation of Gold Catalysts for the Selective Oxidation of Carbohydrates

Preparation of an $Au/TiO_2$ Catalyst (0.45% Au)

The support material employed was an anatase-containing $TiO_2$ hydrate (Kronos, $S_{BET}$=288 $m^2/g$). 500 mg of tetrachloroauric acid ($HAuCl_4 \times 3 H_2O$) in 250 ml of water are added dropwise to an aqueous suspension of 50 g of $TiO_2$ in one liter of distilled water, which has been heated to 70° C. and adjusted to a pH of 6.5 with 0.2 N NaOH, at a constant pH with vigorous stirring over the course of 3 h. The mixture is stirred at 70° C. for a further hour. After cooling to room temperature, a magnesium citrate solution (2.318 g of MgHC$_6$H$_5$O$_7$×5 H$_2$O in 50 ml of water), whose pH has previously been adjusted to 6.5 with 0.2 N NaOH, is added. After stirring for 1 hour, the solid is removed by centrifugation, washed three times with water and then dried in a vacuum drying oven under a pressure of <50 hPa at room temperature for 17 h and at 50° C. for 4 h. The resulting precursor is ground lightly in a mortar and heated in air at a heating rate of 1 K/min to 250° C. and activated at this temperature for 3 h.

Yield: 47.3 g

TEM: particles with d<5 nm predominate, a few particles with d of about 20 nm

ICP-OES analysis: 0.45%

Preparation of an Au/TiO$_2$ Catalyst (3% Au)

TiO$_2$ P25 (Degussa) which consists of 70% anatase and 30% rutile (S$_{BET}$=50 m$^2$/g) was employed as support material.

1.32 g of tetrachloroauric acid (HAuCl$_4$×3 H$_2$O) in 200 ml of water are added dropwise to an aqueous suspension of 20 g of TiO$_2$ in 400 ml of distilled water, which has been heated to 70° C. and adjusted to a pH of 6.5 with 0.2 N NaOH, while stirring vigorously at constant pH over the course of 2.5 h. The mixture is stirred at 70° C. for 1 h. After cooling, a magnesium citrate solution (6.118 g of MgHC$_6$H$_5$O$_7$×5 H$_2$O in 100 ml of water), whose pH has previously been adjusted to 6.5 with 0.2 N NaOH, is added. After stirring for 1 hour, the solid is removed by centrifugation, washed three times with water and dried in a vacuum drying oven under a pressure of <50 hPa at room temperature for 16 h and at 50° C. for 4 h and then ground lightly in a mortar. The resulting precursor is heated in air at a heating rate of 1 K/min to 250° C. and activated at this temperature for 3 h.

Yield: 20.5 g

TEM: regularly distributed small particles with d=1-4 nm

ICP-OES analysis: Au content=3.03%

Preparation of an Au/TiO$_2$ Catalyst (1% Au)

An anatase-containing TiO$_2$ hydrate (Kronos) which was calcined at 400° C. for 5 h before being loaded with a polymer-stabilized gold sol solution (S$_{BET}$=130 m$^2$/g) was used as support material.

2 ml of 0.1 N NaOH were added dropwise to a solution consisting of 80 mg of tetrachloroauric acid (HAuCl$_4$×3 H$_2$O) in 400 ml of water. While stirring vigorously, the colloid-stabilizing polymer (120 mg of polydiallyldimethylammonium chloride, MW=100 000 to 200 000, 20% strength in water, diluted with 4 ml of water) was added. After reduction of the gold (III) ions with sodium borohydride (76 mg of NaBH$_4$ in 4 ml of water), immediately 4 g of the prepared TiO$_2$ were added while stirring vigorously. After stirring for one hour, the catalyst was removed by centrifugation, washed three times with water and dried in a vacuum drying oven under a pressure of <50 hPa at room temperature for 17 h and at 50° C. for 4 h.

Yield: 4 g

ICP-OES analysis: Au content=1%

Preparation of an Au/Al$_2$O$_3$ Catalyst (0.95% Au)

Puralox HP 14/150 (Sasol/Condea) with S$_{BET}$=151 m$^2$/g was used as Al$_2$O$_3$ support material.

900 mg of tetrachloroauric acid (HAuCl$_4$×3 H$_2$O) in 450 ml of water are added dropwise to an aqueous suspension of 30 g of Al$_2$O$_3$ in 600 ml of distilled water, which has been heated to 70° C. and adjusted to a pH of 7 with 0.1 N NaOH, while stirring vigorously over the course of 3 h at constant pH. The reaction solution is stirred further at 70° C. for 1 h. The mixture is cooled to room temperature and a magnesium citrate solution (4.172 g of MgHC$_6$H$_5$O$_7$×5 H$_2$O in 90 ml of water) whose pH had previously been adjusted to 7 with dilute NaOH is added thereto. After stirring for 1 hour, the solid is removed by centrifugation, washed three times with water and dried in a vacuum drying oven under a pressure of <50 hPa at room temperature for 17 h and at 50° C. for 4 h, and then ground lightly in a mortar. The resulting precursor is heated in air at a heating rate of 1 K/min to 250° C. and activated at this temperature for 3 h.

Yield: 27.3 g

TEM: particles with d=1-2 nm predominate

ICP-OES analysis: Au content=0.95%

What is claimed is:

1. A method for the selective oxidation of at least one carbohydrate, a carbohydrate mixture or a composition having a content thereof, where an aqueous solution of the carbohydrate, of the mixture or of the composition is reacted in the presence of a gold catalyst comprising nanodispersed gold particles having a diameter of less than 20 nm on a metal oxide support, and of oxygen, where an aldehyde group on the C1 carbon atom of the carbohydrate(s) is selectively oxidized to a carboxyl group, or an aldehyde group is introduced on the C1 carbon atom and selectively oxidized to a carboxyl group.

2. The method as claimed in claim 1, where the metal oxide support of the gold catalyst is a TiO$_2$ support.

3. The method as claimed in claim 2, where the TiO$_2$-supported gold catalyst comprises about 0.1% to 5% gold.

4. The method as claimed in claim 1, where the metal oxide support of the gold catalyst is an Al$_2$O$_3$ support.

5. The method as claimed in claim 4, where the Al$_2$O$_3$-supported gold catalyst comprises about 0.1% to 5% gold.

6. The method as claimed in claim 1, where the oxidation is carried out at a pH of from 7 to 11.

7. The method as claimed in claim 1, where the oxidation is carried out at a temperature of from 20° C. to 140° C.

8. The method as claimed in claim 1, where the oxidation is carried out under a pressure of from 1 bar to 25 bar.

9. The method as claimed in claim 1, where at least one of oxygen and air is bubbled through the aqueous solution of the carbohydrate, of the mixture or of the composition during the oxidation.

10. The method as claimed in claim 1, wherein the carbohydrate to be oxidized is an aldose having an aldehyde group on the C1 carbon atom.

11. The method as claimed in claim 1, wherein the carbohydrate to be oxidized is in the 2-ketose form which is initially converted into the oxidizable tautomeric aldose form.

12. The method as claimed in claim 10, where the carbohydrate to be oxidized is a monosaccharide, an oligosaccharide, a mixture thereof or a composition having a content thereof.

13. The method as claimed in claim 10, where the monosaccharide to be oxidized is glucose, galactose, mannose, xylose or ribose.

14. The method as claimed in claim 13, where gluconic acid is obtained as oxidation product in the oxidation of glucose.

15. The method as claimed in claim 12, where the oligosaccharide to be oxidized is a disaccharide.

16. The method as claimed in claim 15, where the disaccharide is a disaccharide aldose.

17. The method as claimed in claim 16, where maltobionic acid is obtained as oxidation product in the oxidation of maltose.

18. The method as claimed in claim 16, where lactobionic acid is obtained as oxidation product in the oxidation of lactose.

19. The method as claimed in claim 15, where the disaccharide is a disaccharide 2-ketose.

20. The method as claimed in claim 12, where the carbohydrate to be oxidized is maltodextrin.

21. The method as claimed in claim 12, where the carbohydrate to be oxidized is a starch syrup.

22. A method for the selective oxidation of at least one oligosaccharide, a mixture thereof or a composition having a content thereof, where an aqueous solution of the oligosaccharide, of the mixture or of the composition is reacted in the presence of a gold catalyst comprising nanodispersed gold particles having a diameter of less than 20 nm on a metal oxide support, and of oxygen, where an aldehyde group on the C1 carbon atom of the carbohydrate(s) is selectively oxidized to a carboxyl group, or an aldehyde group is introduced on the C1 carbon atom and selectively oxidized to a carboxyl group.

23. The method as claimed in claim 22, where the support of the gold catalyst employed is a $TiO_2$ support.

24. The method as claimed in claim 23, where the $TiO_2$-supported gold catalyst comprises about 0.1% to 5% gold.

25. The method as claimed in claim 22, where the support of the gold catalyst employed is an $Al_2O_3$ support.

26. The method as claimed in claim 25, where the $Al_2O_3$-supported gold catalyst comprises about 0.1% to 5% gold.

27. The method as claimed in claim 22, where the oxidation is carried out at a pH of from 7 to 11.

28. The method as claimed in claim 22, where the oxidation is carried out at a temperature of from 20° C. to 140° C.

29. The method as claimed in claim 22, where the oxidation is carried out under a pressure of from 1 bar to 25 bar.

30. The method as claimed in claim 22, where at least one of oxygen and air is bubbled through the aqueous solution of the oligosaccharide, of the mixture or of the composition during the oxidation.

31. The method as claimed in claim 22, where the oligosaccharide to be oxidized is an aldose having an aldehyde group on the C1 carbon atom.

32. The method as claimed in claim 31, where the oligosaccharide to be oxidized is a disaccharide aldose.

33. The method as claimed in claim 32, where the disaccharide aldose is maltose, lactose, cellobiose or isomaltose.

34. The method as claimed in claim 33, where maltobionic acid is obtained as oxidation product in the oxidation of maltose.

35. The method as claimed in claim 33, where lactobionic acid is obtained as oxidation product in the oxidation of lactose.

36. The method as claimed in claim 22, where the oligosaccharide to be oxidized is in the 2-ketose form which is converted into the oxidizable tautomeric aldose form before the oxidation.

37. The method as claimed in claim 36, where the oligosaccharide to be oxidized is a disaccharide 2-ketose.

38. The method as claimed in claim 37, where the disaccharide ketose is palatinose.

39. The method as claimed in claim 22, where the oligosaccharide mixture to be oxidized is maltodextrin.

40. The method as claimed in claim 22, where the composition to be oxidized is a starch syrup.

41. The method as claimed in claim 3, wherein the $TiO_2$-supported gold catalyst comprises about 0.5% to 1% gold.

42. The method as claimed in claim 5, wherein the $Al_2O_3$-supported gold catalyst comprises about 0.5% to 1% gold.

43. The method as claimed in claim 16, wherein the disaccharide is selected from the group consisting of maltose, lactose, cellobiose and isomaltose.

44. The method as claimed in claim 19, wherein the disaccharide is palatinose.

45. The method as claimed in claim 24, wherein the $TiO_2$-supported gold catalyst comprises about 0.5% to 1% gold.

46. The method as claimed in claim 26, wherein the $Al_2O_3$-supported gold catalyst comprises about 0.5% to 1% gold.

47. The method as claimed in claim 7, wherein the oxidation is carried out at a temperature of from 40° C. to 90° C.

48. The method as claimed in claim 28, wherein the oxidation is carried out at a temperature of from 40° to 90° C.

* * * * *

UNITED STATES PATENT AND TRADEMARK OFFICE
CERTIFICATE OF CORRECTION

PATENT NO. : 7,982,031 B2  
APPLICATION NO. : 10/555714  
DATED : July 19, 2011  
INVENTOR(S) : Jörg Kowalczyk et al.

Page 1 of 1

It is certified that error appears in the above-identified patent and that said Letters Patent is hereby corrected as shown below:

Title Page,

Item (73) Assignee should read:

Südzucker Aktiengesellschaft Mannheim/Ochsenfurt (DE)

Signed and Sealed this
Eighteenth Day of October, 2011

David J. Kappos
*Director of the United States Patent and Trademark Office*